(12) United States Patent
Ito

(10) Patent No.: US 6,391,019 B1
(45) Date of Patent: May 21, 2002

(54) VALVE APPARATUS AND VALVE SYSTEM USING THEREOF

(75) Inventor: Takashi Ito, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/675,228

(22) Filed: Sep. 29, 2000

(30) Foreign Application Priority Data

Oct. 4, 1999 (JP) ............................................. 11-283446

(51) Int. Cl.[7] ............................ A61K 9/22; A61M 5/00; F16K 31/08; F16K 25/00; F16K 17/00
(52) U.S. Cl. .......................... 604/891.1; 604/9; 251/65; 251/177; 251/233; 251/234; 137/524; 137/530; 137/531
(58) Field of Search .......................... 251/65, 176, 177, 251/228, 233, 234; 137/426, 524, 530, 531; 604/9, 891.1

(56) References Cited

U.S. PATENT DOCUMENTS

| | | | |
|---|---|---|---|
| 1,462,081 A | * | 7/1923 | Breeden |
| 4,387,715 A | * | 6/1983 | Hakim et al. .................. 604/9 |
| 4,595,390 A | * | 6/1986 | Hakim et al. .................. 604/9 |
| 4,615,691 A | * | 10/1986 | Hakim et al. .................. 604/9 |
| 4,772,257 A | * | 9/1988 | Hakim et al. .................. 604/9 |
| 5,928,182 A | * | 7/1999 | Kraus et al. .................. 604/9 |
| 6,050,696 A | * | 4/2000 | Kraus ........................... 604/9 |

* cited by examiner

*Primary Examiner*—Kevin Shaver
*Assistant Examiner*—David A Bonderer
(74) *Attorney, Agent, or Firm*—Adams & Wilks

(57) ABSTRACT

A valve apparatus of a valve system includes a long-sized elastic member a base end portion of which is fixed and a front end portion of which is brought into contact with a valve element and a movable member capable of moving in B1 and B2 directions actually linearly along a longitudinal direction B of the elastic member between both end portions of the elastic member and having a fulcrum portion for flexing the elastic member in C direction between the both end portions of the elastic member. The movable member is constituted by a slider linearly moved in accordance with a mover of a linear step motor element or rotation of a rotor of a rotary type step motor element.

17 Claims, 6 Drawing Sheets

VALVE APPARATUS AND VALVE SYSTEM USING THEREOF

BACKGROUND OF THE INVENTION

1. Field of the Invention

The present invention relates to a valve apparatus, more particularly, to a valve apparatus suitable for being used as a shunt valve embedded in the body for adjusting the pressure of the cerebrospinal fluid or the like and a valve system comprising the valve apparatus and a control device for controlling set pressure of the valve apparatus.

2. Description of the Prior Art

Japanese Patent Laid-Open No. 40063/1985 discloses a constitution in which there is provided in a flow path of the cerebrospinal fluid or the like for adjusting the pressure of the cerebrospinal fluid or the like, a shunt valve provided with a leaf-like spring one end portion of which is brought into contact with a ball serving as a valve element, other end portion of which is engaged with a cam face in a shape of a spiral staircase integrally formed with a rotor of a multiple poles step motor element and which changes press force of a ball by the spring by changing a flexing amount of the spring by moving the engaged end portion of the spring in an axial direction of the rotor in accordance with rotation of the cam face in correspondence with rotation of the rotor for treatment of hydrocephalus or the like.

However, in the case of the shunt valve apparatus, the thickness of the shunt valve apparatus is difficult to increase so considerably since the flexing direction of the spring is aligned to the thickness direction of the valve apparatus and therefore, when a comparatively wide range of pressure adjustment is made feasible by one kind of the shunt valve apparatus, it is necessary to comparatively increase a variation in press force exerted on the ball-like valve element even with a very small flexing amount of the spring and accordingly, even a very small dispersion in the flexing state of the spring is liable to amount to a large dispersion in the press force and it is not necessarily easy to adjust the press force to a predetermined value. Further, in order to change the flexing amount of the spring to adjust set pressure of the shunt valve apparatus, it is necessary to arrange a pressure adjusting or controlling device (shunt valve adjusting element) having a plurality of pieces of electromagnets along a circumferential direction such that the center of the device coincides accurately with the center of the multiple poles step motor element embedded in the body and therefore, the pressure adjustment is difficult to carry out easily.

Further, there is also known in, for example, Japanese Patent Laid-Open No. 170749/1996, a valve apparatus in which one end portion of a leaf spring bent substantially in a semicircular shape is fixed to a rotor having a permanent magnet, a peripheral face of a middle portion of the leaf spring extended to bend in the semicircular shape from the fixed end portion to a free end, is made to be able to be brought into contact with a valve element in a ball-like shape and press force of the ball by the spring is changed in accordance with a change in a position of bringing the spring and the ball into contact with each other in accordance with rotation of the rotor.

However, according to the valve apparatus, in order to be able to accurately adjust the press force exerted to the ball, a leaf spring in a specific bent state in substantially a semicircular shape is indispensable and it is not necessarily easy to realize a two-dimensional shape of such a spring with the least dispersion.

The invention has been carried out in view of the above-described points and it is an object thereof to provide a valve apparatus which is easy to set the press force exerted on a valve element with high accuracy and a valve system including the valve apparatus.

SUMMARY OF THE INVENTION

In order to achieve the object, according to an aspect of the invention, there is provided a valve apparatus comprising a long-sized elastic member a base end portion of which is fixed and a front end portion of which is brought into contact with a valve element, and a movable member movable actually linearly along a longitudinal direction of the elastic member between both end portions of the elastic member and having a fulcrum portion for flexing the elastic member between the both end portions of the elastic member.

According to the valve apparatus of the invention, there is provided the movable member movable actually linearly along the longitudinal direction of the elastic member between the fixed base end portion of the long-sized elastic member and the front end portion brought into contact with the valve element and having the fulcrum portion for flexing the elastic member between the both end portions of the elastic member and accordingly, the press force exerted on the valve element by the elastic member can be adjusted by adjusting the position of the fulcrum portion by adjusting the position of the movable member in the longitudinal direction of the elastic member to thereby change the spring constant of the elastic member between a position of supporting and pressing the elastic member by the fulcrum portion and a position of supporting (contacting) the elastic member by the valve element. Further, the elastic member is long-sized and the position of the movable member is moved in the longitudinal direction of the elastic member in order to change the flexing state of the elastic member and accordingly, an amount of moving the movable member can be increased even for slightly changing the flexing state of the elastic member. Therefore, the flexing state is easy to adjust accurately. Further, the elastic member is fixed at the base end portion and is brought into contact with the valve element at the front end portion and supported by the valve element to thereby bring about a doubly supported state and accordingly, not only the elastic member can be held stably but also a flexing deformation is added at the middle portion in the longitudinal direction of the elastic member in the doubly supported state by the fulcrum portion and therefore, there is less concern of concentrating stress at one portion of the elastic member, the flexing state of the elastic member is easy to control accurately and there is less concern of variation or deterioration in the flexing characteristic of the elastic member even when the elastic member is used for a long period of time.

The elastic member is typically constituted by a leaf spring. However, when desired, the elastic member may be a structure of an elastic member material capable of setting the characteristic of the flexing deformation in a desired manner.

When the elastic member comprises a leaf spring, at least one of a thickness, a width, an inclination and a contour line of a face pressed by the fulcrum portion of the spring may be changed in accordance with a position of the spring in the longitudinal direction such that the press force of the valve element by the spring is varied in a desired pattern in accordance with moving the fulcrum portion in the longitudinal direction of the spring. In this case, the way of varying the press force may be constituted such that when the movable member is moved in a direction of approaching the valve element along the longitudinal direction of the spring, the press force of the valve element by the spring is increased actually linearly or increased sublinearly. Further, a degree of the increase (for example, inclination in the linear case) may be made comparatively large or small. With regard to the width of the spring, the width may be varied such that, for example, the more proximate to the front end portion, the larger the width, or conversely, the smaller the width, the width is varied along the longitudinal direction by other mode (for example, such that the more proximate to the front end portion, the larger the width in a range from a middle predetermined position to the front end portion or the width is large at a central portion in the longitudinal direction and is small at both end sides or the width is small at the central portion in the longitudinal direction and is large at the both end sides or the width is varied periodically at a predetermined pitch along the longitudinal direction). The same goes with the thickness and the thickness may be varied instead of or along with varying the width of the spring along the longitudinal direction or the thickness may be varied by the above-described mode while the width is varied. A total of the thickness in the width direction may be varied or the thickness may be varied such that there is provided a projected shape or a recess groove extended in a desired range along the longitudinal direction at a portion in the width direction. Further, the spring may be fabricated such that while the thickness stays substantially in a constant state, in view of a cross-sectional face orthogonal to the longitudinal direction, a recess portion is formed on one surface and a projected portion is formed on other surface. With regard to the inclination, when the spring is formed in a flat plate shape, the inclination may be constituted such that a relative height between the front end portion and the base end portion of the spring is changed and the spring is actually extended in a direction in parallel with the direction of moving the movable member on a front end side or a base end side of a position of supporting the spring by the fulcrum portion or the spring may be inclined slightly in the direction of moving the movable member in either of the directions. In the case of the spring in the flat plate shape, a change in the inclination amounts to a change in the contour of the upper face of the spring. Meanwhile, the contour of the upper face may be changed by changing the thickness of the spring.

The fulcrum portion may be a protruded portion or a projected portion formed at a position of the movable member opposed to one face of the elastic member or may be a rolling element such as a ball or a roller rollably contained and supported by a main body portion of the movable member. A front end of the protruded portion or the projected portion which is brought into contact with the surface of the elastic member for pressing the surface, may be formed in a dot-like shape or a linear shape extended in a direction intersecting with the longitudinal direction of the elastic member, typically, a direction orthogonal thereto. A length of projecting the fulcrum portion from the main body portion of the movable member to the surface or the spring is typically maintained constant. However, when desired, the projected length per se may be varied in accordance with the position of the movable portion along the longitudinal direction of the spring. Typically, the fulcrum portion is projected from a surface of the main body portion of the movable member opposed to a pressed face of the elastic member. However, when desired, an arm portion may be provided at the main body portion of the movable member and the fulcrum portion may be provided at the arm portion.

The valve element is typically constituted by a ball. However, when desired, the valve element may be formed in other shape.

The movable member is typically constituted by a slider slidable along a wall of the valve apparatus main body. However, the movable member may penetrate the wall of the valve apparatus main body or a guide shaft via a rollable ball or the like and may be movable relative to the guide shaft. The movable member may be constituted by a mover, that is, a moving piece of a linearly driven step motor element or may be coupled to a conversion mechanism for converting rotation of a rotor of a step motor element of a rotary type into linear motion. Further, the motor is an electric motor and is preferably constituted by a step motor element such that the position of the movable member is easy to control firmly from outside. However, when desired, the motor may be constituted by other kind of motor. Further, the step motor element is preferably constituted to be magnetized in a direction orthogonal to the longitudinal direction of the elastic member. In that case, by applying a pulse-like magnetic field which is spatially uniform in a direction orthogonal to a direction of extending the elastic member from outside, the position of the movable member can be changed by driving the step motor element via the stator and accordingly, positioning of a drive source relative to the step motor element can be carried out easily and firmly. Further, the step motor element is preferably constituted to produce force for holding the movable member at a stationary position when the stator is not applied with the magnetic field. In that case, there is less concern of varying the position of the movable member by mechanical impact, magnetic or electromagnetic disturbance or the like from outside or the variation of the position can be minimized.

Although the valve apparatus may be used other than the field applied to the human body such as medical use or the like, typically, the valve apparatus is constituted to be able to surgically embed into the body to be used as a shunt valve, for example, for the ventricle of the brain —the abdominal cavity shunt, the ventricle of the bran —the ventricle of the heart shunt or the like such that pressure of a related fluid in the body can be noninvasively adjusted with a purpose of treatment of hydrocephalus, cerebral tumor, subarachnoid cyst or the like and can have a size of about several cm or smaller suitable for being used in adjusting the pressure of the cerebrospinal fluid or the like.

The above-described valve apparatus is preferably used by being combined with a movable member position control device in which a stator of a step motor element is applied with a pulse-like magnetic field which is directed in a direction actually orthogonal to the longitudinal direction of the elastic member and which is actually uniform over an entire length in the direction of moving the movable member in order to move the movable member in the longitudinal direction of the spring to thereby constitute a valve system. In this case, control of the position of the movable member can be carried out firmly by applying a desired magnetic field on the stator by only arranging the movable member position control device a direction of which is aligned to the surface of the body such that a pulse-like magnetic field is applied in the direction orthogonal to the longitudinal direction of the elastic member.

BRIEF DESCRIPTION OF THE DRAWINGS

A preferred form of the present invention is illustrated in the accompanying drawings in which.

DETAILED DESCRIPTION OF THE PREFERRED EMBODIMENTS

Next, an explanation will be given of several preferable modes of carrying out the invention based on embodiments shown in the attached drawings.

Figure 1:
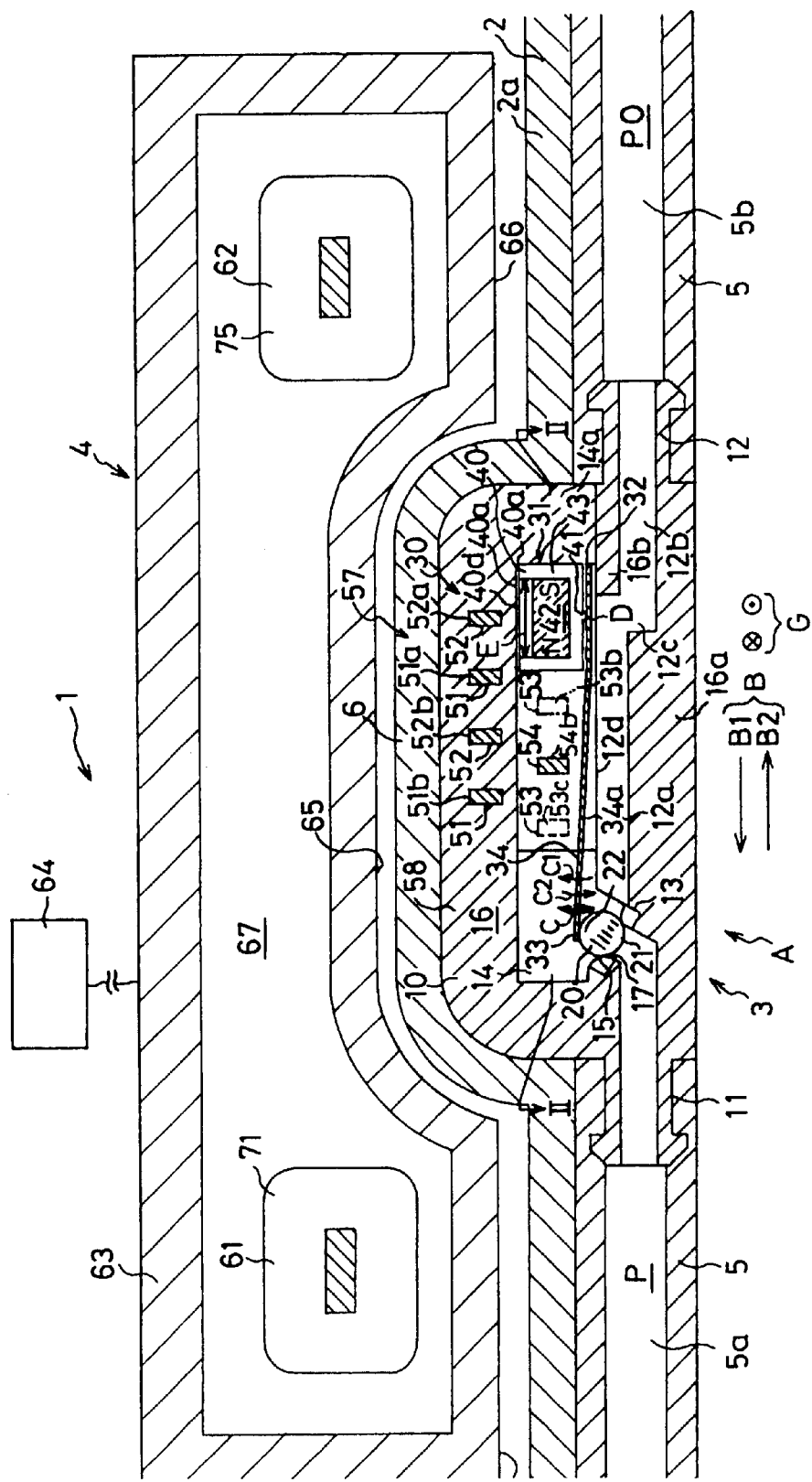
FIG. 1 shows a valve system of a preferable embodiment according to the invention which is applied to the human body and is an explanatory view of a section taken along a line I—I of FIG. 2 (however, stator pole pieces on this side are shown by imaginary lines)
Figure 2:
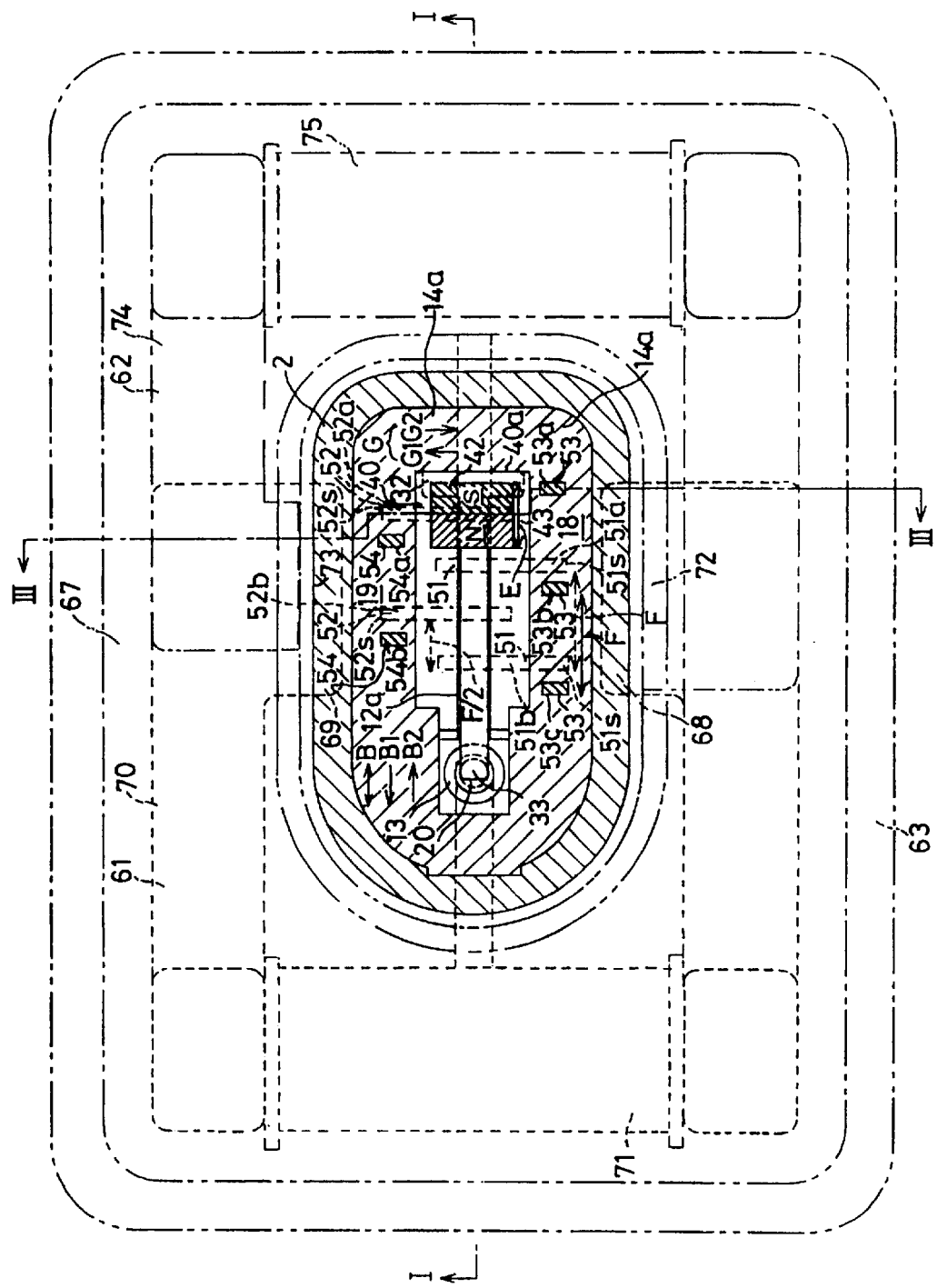
FIG. 2 is an explanatory view of a section taken along a line II—II of the valve system of FIG. 1 (however, stator pole pieces disposed above are shown by broken lines, related electromagnets are similarly shown by broken lines and other portions of a control device are added by imaginary lines)
Figure 3:
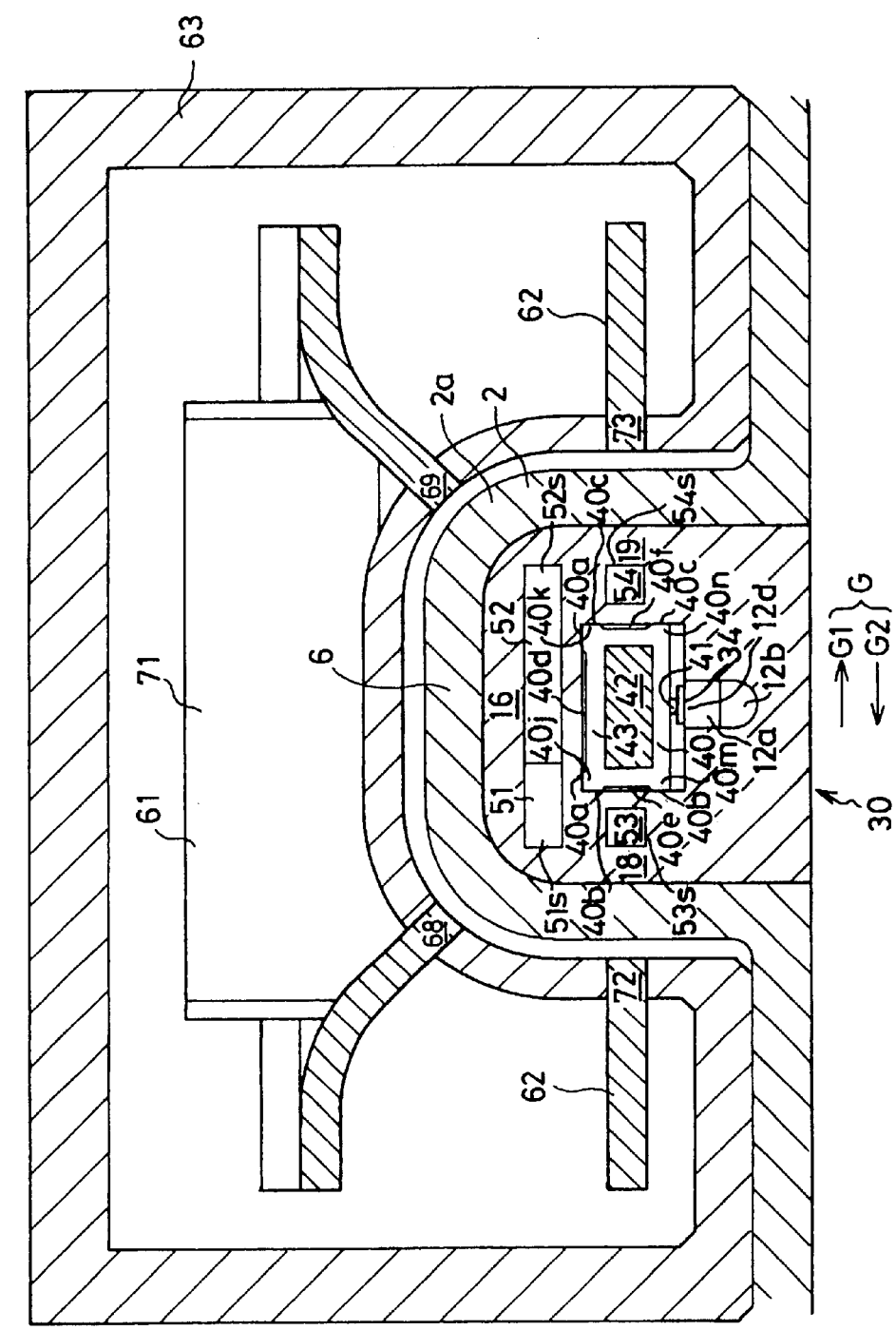
FIG. 3 is an explanatory view of a section taken along a line III—III of FIG. 2 with regard to the valve system of FIG. 1.

First, FIGS. 1 through 3 show a valve system 1 of a first embodiment in a state in which the valve system 1 is applied to the human body for simply clarifying the explanation.

The valve system is constituted by a valve apparatus 3 embedded in the human body 2 and a pressure adjusting and controlling apparatus 4 and the pressure adjusting and controlling apparatus 4 adjusts pressure $\Delta P$ adjusted or set by the valve apparatus 3.

The valve apparatus 3 is arranged at, for example, a portion A at a middle of a conduit 5 of the cerebrospinal fluid for setting and adjusting the pressure P of the cerebrospinal fluid at an upstream conduit portion 5a such that the pressure P does not become higher than pressure P0 of the cerebrospinal fluid at a downstream side conduit portion 5b by a set pressure $\Delta P$ of the valve apparatus 3 or higher. That is, the pressure P of the cerebrospinal fluid is set and adjusted to be equal or lower than $P0+\Delta P$. For example, in the case in which the pressure P0 actually coincides with the atmospheric pressure, when P0=0 with the atmospheric pressure as a reference, $P=\Delta P$. Further, the valve apparatus 3 may be used as a valve apparatus for adjusting pressure such that the pressure of the downstream side conduit portion 5b becomes equal to or higher than predetermined pressure $P0(=P-\Delta P)$.

The valve apparatus 3 is provided with an entry side and an outlet side conduit portion 11 and 12, a chamber 14 communicating with the outlet side conduit portion 12 and an opening 17 for connecting the entry side conduit portion 11, the outlet side conduit portion 12 and the chamber 14 at inside thereof and is provided with a valve apparatus main body or a valve housing 10 comprising silicone resin, polycarbonate or the like, a valve member or a valve element 20 in a shape of a ball made of hard ceramic such as sapphire, ruby or the like for opening and closing the opening 17 in the valve apparatus main body 10 and a pressure adjusting mechanism 30 for releasing closure of the flow path 17 by the ball valve 20 in cooperation with the ball valve 20 when the pressure P of the upstream side conduit 5a exceeds the set pressure $P0+\Delta P$. According to the valve housing 10, for example, the width is about several mm through 2 cm, the length is about several mm through 5 cm and the height is about several mm through 1 cm. However, sizes in the respective directions may be smaller or larger depending on cases.

More in details, the valve apparatus main body 10 is provided with the inlet side conduit portion 11 connected to the upstream side conduit portion 5a, the outlet side conduit portion 12 connected to the downstream side conduit portion 5b, a valve seat portion 13 on which the ball valve 20 can be seated between the inlet side and the outlet side conduit portions 11 and 12 and which comprises a material similar to that of the ball 20 and the chamber 14 containing the ball valve 20 and a main body portion 31 of the pressure adjusting mechanism 30. The outlet side conduit portion 12 is provided with a first conduit portion 12a disposed just downstream from the ball valve 20, a second conduit portion 12b communicating with the downstream side cerebrospinal fluid conduit portion 5b and a connection tube portion 12c extended in the up and down direction in FIG. 2 between the first and the second conduit portions 12a and 12b and the first conduit portion 12a and the connection tube portion 12 comprise a groove formed at a bottom wall 16a of the chamber 14. The valve seat portion 13 comprises a valve seat member having a seat face 15 in a shape of a fulcrum of a circular cone.

The main body portion 31 of the pressure adjusting mechanism 30 is provided with a leaf spring 34 in a flat plate shape one end 32 of which is fixed to the valve apparatus main body 10 and other end 33 of which is extended from the end portion 32 in B direction and is brought into contact with the ball 20 and a fulcrum position changing member or movable member 40 for pressing and flexing the leaf spring 34 by a fulcrum projection 41 at a middle portion of the spring 34 between the doubly supported end portions 32 and 33 to change a flexing state of the leaf spring 34 in C direction. The spring 34 comprises a nonmagnetic metal material such as, for example, nonmagnetic stainless steel, the width is about 1 mm, the thickness is about 0.1 mm and the length is about 1 through 2 cm. However, sizes in the respective directions may be smaller or larger depending on cases. As shown by FIG. 3, the movable member 40 is provided with recess portions 40d, 40e and 40f permitting to pass the physical fluid such as the cerebrospinal fluid at central portions of a top face 40a and both side faces 40b and 40c and can move forward and move backward in B1 and B2 directions (summarizingly referred to by notation B) in a state in which the faces 40a, 40b and 40c constituting four corners 40j, 40k, 40m and 40n, are brought into sliding contact with a top wall 16 and both side walls 18 and 19 of the chamber 14 except that a bottom face 40h is supported by the spring 34 at the projection 41. Further, a ball bearing made of ceramic may be provided between the movable member 40 and the valve apparatus main body 10 and the movable member 40 may be made rollable relative to the valve apparatus main body 10 at the bearing ball portion. Although in FIG. 3, the fulcrum projection 41 is shown in a projected shape extended in G direction, the projected shape may be in a dot-like shape also in G direction. Further, G direction and B direction are directions orthogonal to each other and disposed on a horizontal face in the state shown by FIGS. 1 through 3. Although in the following explanation, with apparent directions of FIGS. 1 through 3 as the bases, technical terms of horizontal direction and up and down direction are used, it is apparent that these directions can be varied depending on directions of the human body 2 embedded with the valve apparatus 3.

The spring 34 exerts press force to the ball 20 in a direction C2 of closing the opening 17 between the peripheral face of the ball 20 and the valve seat face 15 at a portion 22 of the ball 20 on a side actually opposed to a portion 21 in contact with the valve seat 13. Typically, the spring 34 is only fixed to an upper side wall 16b of the conduit 12b constituting an upper bottom wall of the chamber 14 of the valve apparatus main body 10 at the base end portion 32 (FIG. 2) having a width in G direction substantially the same as that of the movable member 40 and is not brought into contact with the bottom walls 16a and 16b of the chamber 14 but separated from the wall portions 16a and 16b at a middle portion shifted from the end portion 32 in B1 direction. As is apparent from FIGS. 1 and 3, in this example, the partition wall 16b for separating the chamber 14 from the conduit 12a is not present at the conduit portion 12a and the connection tube portion 12c, an upper side end of the conduit 12a is exposed to the chamber 14 at an opening 12d and the width of the spring 34 (length in G direction) is slightly smaller than the width of the conduit portion 12a. Therefore, the spring 34 is doubly supported by the end portions 32 and 33 and is pressed at a portion D by the fulcrum projection 41. However, when desired, the partition wall 16b constituting a top wall of the conduit portion 12a may be formed at a total of the chamber 14. However, in that case, it is preferable that a gap remains between the partition wall 16a and the spring 34 in a region between the fulcrum position D and the fixed base end portion 32 to avoid stress from being concentrated excessively at the fulcrum position D pressed by the fulcrum 41 of the movable member 40. Further, it is preferable that the gap is comparatively large to avoid the physical fluid in the chamber 14 from staying in the gap.

The movable member 40 is constituted by embedding a permanent magnet 42 having a length E (for example, about 2 through 3 mm) magnetized in B1 direction in a movable housing 43 as a movable member main body comprising silicone resin, polycarbonate or the like and the fulcrum projection 41 is formed at a bottom portion of the housing 43. The permanent magnet 42 comprising a hard magnetic material such as Sm—Co series alloy may be constituted by a single member or may be constituted by laminating a plurality of magnets in the same magnetizing direction as shown by FIG. 2 and direction of magnetization of the magnet 42 may be in B2 direction reverse to the illustrated.

The top wall 16 and the both side walls 18 and 19 of the valve apparatus main body 10, are embedded with a plurality or a number of two sets and four groups of stator pole pieces 51, 52 and 53, 54 each comprising a soft magnetic member magnetically such as permalloy having high permeability at predetermined intervals F in B direction. Here, a technical term of ferromagnetism is in a broad sense including ferrimagnetism or the like.

More in details, the stator pole pieces 51 embedded in the top wall 16 at intervals F, are extended from a vicinity of surface of the side wall 18 in G direction orthogonal to B direction actually over an entire width of the permanent magnet 42. It is preferable that respective end portions of the stator pole piece 51 disposed at vicinities of the surface of the housing 43 are extended to locations as proximate to the surface as possible so far as the seal state of the chamber 14 and the conduit portion 12 can be maintained firmly (same goes with also other stator pole piece, mentioned later). FIG. 2 shows two of such stator pole pieces 51 by notations 51a and 51b. Similarly, the stator pole pieces 52 embedded in the top wall 16 at the interval F are extended from vicinities of surface of the side wall 19 in G direction orthogonal to B direction and extended substantially over the total width of the permanent magnet 42. FIG. 2 shows two of such stator pole pieces 52 by notations 52a and 52b. The stator pole pieces 51a, 52a, 51b and 52b are disposed equally at intervals E=F/2 actually coinciding with the distance or the length E between magnetic poles of the magnet 42. That is, the stator pole piece 51a is disposed just at middle of the stator pole pieces 52a and 52b in B direction, the stator pole piece 52b is disposed just at middle of the stator pole pieces 51a and 51b and the distance between the stator pole pieces 51 and 52 in B direction which are contiguous in B direction, actually coincides with the length E=F/2 of the permanent magnet 42 of the mover 40.

Similarly, the stator pole pieces 53 embedded in the side wall 18 at intervals F in B direction, are extended in G direction from a vicinity of an outer surface of the side wall 18 to a vicinity of an inner surface thereof. FIG. 2 shows three of such stator pole pieces 53 by notations 53a, 53b and 53c. Further, the stator pole pieces 54 embedded in the side wall 19 at intervals F are extended in G direction from a vicinity of an outer surface of the side wall 19 to a vicinity of an inner surface thereof. FIG. 2 shows two of such stator pole pieces 54 by notations 54a and 54b. The stator pole pieces 53a, 54a, 53b, 54b and 53c are also disposed at equal intervals by the interval E=F/2 actually coinciding with the distance or the length E between the magnetic poles of the magnet 42, the stator pole piece 53b is disposed just middle of the stator pole pieces 54a and 54b, the stator pole pics 54a is disposed just middle of the stator pole pieces 53a and 53b and the stator pole piece 54b is disposed just middle of the stator pole pieces 53b and 53c and the distance in B direction between the stator pole pieces 53 and 54 which are contiguous in B direction, actually coincides with the length E=F/2 of the permanent magnet 42 of the mover 40.

Further, intervals among the stator pole pieces 53a, 52a, 54a, 51a, 53b, 52b, 54b, 51b and 53c which are mostly contiguous in B direction, are the same and E/2. Further, according to the mover 40 having the permanent magnet 42, in an initial state in which the end face 40a in B2 direction is brought into contact with a side wall 14a of the chamber 14, S pole of the magnet 42 is disposed at a position mostly proximate to the stator pole piece 53a, N pole is disposed at a position mostly proximate to the stator pole piece 54a and at the positions, a magnetic path for magnetizing the stator pole pieces 53a and 54a is formed, the permanent magnet 42 is brought into a state of being attracted to the two stator pole pieces 53a and 54a and there is exerted hold force for holding the mover 40 at the positions. Further, at this occasion, the stator pole piece 52a is disposed just at center of the two magnetic poles of the permanent magnet 42 and almost no force is exerted actually between the stator pole piece 52a and the permanent magnet 42. Further, a distance between the other stator pole piece and the permanent magnet 42 is comparatively large and therefore, a force by t he other stator pole piece exerted on the mover 40 via the permanent magnet 42, is actually negligible in comparison with the force exerted by the stator pole pieces 53a and 54a on the mover 40. Such a position of holding the mover 40 is realized similarly at each pitch of E/2 in B direction from the initial position by similar reason and accordingly, even in a state in which the stator pole piece is not magnetized from outside, the mover 40 is provided with stable hold positions at pitch of E/2.

Further, in changing a number of the hold positions, a number of the respective stator hole pieces 51, 52, 53 and 54 may be changed and in changing intervals among the hold positions, the length E in B direction of the magnet 42 and the interval E/2 between the contiguous stator pole pieces may be changed. A stator 58 for forming a linear step motor element 57 in cooperation with the mover 40, comprises the stator pole pieces 51, 52, 53 and 54 embedded in the wall portions 16, 18 and 19 of the housing 10.

The pressure adjusting and controlling apparatus 4 as a mover position control apparatus for controlling the position of the mover 40 by controlling operation of the step motor element 57, is constituted by a first and a second electromagnet 61 and 62, a control device housing 63 containing the electromagnets 61 and 62 and a power feed control unit 64 (FIG. 1) for feeding power to the electromagnets 61 and 62.

The control device housing 63 is provided on base 66 with a recess portion 65 in a slender shape substantially complementary to an eminence portion 6 of the scalp or the like constituting a contour shape substantially coinciding with the contour shape of the valve apparatus main body 10 at the head portion embedded with the valve apparatus 3. The first electromagnet 61 arranged in a chamber 67 of the control device housing 63, is provided with magnetic poles 68 and 69 at positions directed from both sides of the eminence portion 6 to outer side end portions of the stator magnetic pole pieces 51 and 52 or the contiguous end portions 51s and 52s when the control device housing 63 is arranged at a predetermined position where the eminence portion 6 is kept in the recess portion 65 of the control device housing 63 and is provided with coil 71 wound at a middle portion of a yoke or magnetic core 70 connecting the magnetic poles 68 and 69. Although illustrated on an enlarged scale for for clarity and ease of understanding in FIG. 2 or FIG. 3, in the case of the apparatus of the embodiment, distances between the magnetic poles 68 and 69 of the electromagnet 61 and the contiguous end portions 51s and 52s of the stator poles pieces 51 and 52, are, for example, about 1 mm and the magnetic gap is extremely small. When the magnetic pole 68 is arranged at the illustrated predetermined position, the magnetic pole 68 may be provided with a width capable of being opposed to end portions of the pole pieces such that a magnetic field can be applied to magnetize the stator pole pieces 51a and 51b having an anisotropy of shape in G direction, for example, may be smaller than that shown in FIG. 2. Similarly, when the magnetic pole 69 is arranged at the illustrated predetermined position, the magnetic pole 69 may be provided with a width capable of being opposed to end portions of the pole pieces such that a magnetic field can be applied to magnetize in G direction the stator pole pieces 52a and 52b having an anisotropy of shape in G direction and may be smaller than that shown by FIG. 2.

Similarly, the second electromagnet 62 in the chamber 67 is provided with magnetic poles 72 and 73 extended in G direction at positions directed from both sides of the eminence portion 6 to outer side end portions or the contiguous end portions 53s and 54s of the stator pole pieces 53 and 54 when the control device housing 63 is arranged and is provided with a coil 75 wound at a middle portion of a yoke 74 connecting the magnetic poles 72 and 73. Although illustrated on an enlarged scale for clarity and ease of understanding in FIG. 2 or 3, distances between the magnetic poles 72 and 73 of the electromagnet 62 and the contiguous end portions 53s and 54s of the stator magnetic pieces 53 and 54 are also, for example, about 1 mm in the case of the apparatus of the embodiment. The magnetic pole 72 is provided with a width capable of being opposed to end portions of the pole pieces such that a magnetic field in G direction can be applied to the stator pole pieces 53a, 53b and 53c when the magnetic pole 72 is arranged at the illustrated predetermined position. Further, when the magnetic pole 73 is arranged at the illustrated predetermined position, the magnetic pole 73 may be provided with a width capable of being opposed to the end portions of the magnetic pieces such that the magnetic field in G direction can be applied to the stator pole pieces 54a and 54b and is provided with, for example, a width to a degree shown in FIG. 2. Although in the illustrated example, for easy to understand the explanation, the widths of the magnetic pieces 72 and 73 are made to differ from each other, it is preferable that the widths are to the same degree to make intensities of the magnetic field at vicinities of the two magnetic pieces to the same degree.

Assume that in the valve system or the pressure regulating and controlling system 1 having the pressure or movable position control apparatus 4 constituted as described above, for example, the mover 40 stays under the initial state shown by FIGS. 1 and 2. In the case in which the electromagnets 61 and 62 are not excited by the controller 4, as described above, the mover 40 under the initial state is exerted with holding force to be held at the initial position in cooperation with the stator pole pieces 53a and 54a and can be held at the position comparatively stably even when the human body 2 is applied with impact accompanied by inertia force to accelerate the human body 2 or comparatively large magnetic field in B direction or in the up and down direction of FIG. 1. Further, with regard to a magnetic field which is uniform in G direction, even in the case in which the magnetic field is larger than a magnetic field applied on the contiguous stator pole piece by the magnet 42, in one direction inherent to the respective stable position of the mover 40, force for holding the mover 40 at the position to some degree can be exerted.

For moving the mover 40 in B1 direction, power is fed to the coil 71 of the first electromagnet 61 such that the first electromagnet 61 is excited by the power feed controller 64 in a direction by which the magnetic pole 68 of the first electromagnet 61 constitutes S pole and the magnetic pole 69 constitutes N pole. Thereby, the stator pole pieces 51a and 52a are magnetized in G2 direction and the permanent magnet 42 of the mover 40 magnetized in B1 direction, and the mover 40 is exerted with attractive force in B1 direction by the stator pole piece 51a magnetized such that the front end side region thereof in G1 direction constitutes S pole, at N pole of a front end thereof and is moved in B1 direction by E/2. Further, when the mover 40 is moved from the initial position in B1 direction even slightly, attractive force exerted to S pole of the magnet 42 of the mover 40 by N pole of an end portion in G2 direction of the stator pole piece 52a magnetized in G2 direction, is increased and the force also contributes to moving the mover 40 in B1 direction by E/2.

When the two magnetic poles of the permanent magnet 42 of the mover 40 reach positions respectively opposed to the stator pole pieces 51a and 52a, a force hampering further displacement is exerted by the two pole pieces and accordingly, the mover 40 is not moved further in B1 direction. Further, even when the excitation is stopped, magnetic poles N and S of the permanent magnet 42 are opposed to the stator pole pieces of a and 52a and magnetize these pole pieces to thereby exert attractive force to each other and accordingly, the mover 40 is held at the position.

Next, excitation of the first electromagnet 61 is stopped and power is fed to the coil 75 of the second electromagnet 62 by the power feed controller 64 such that the second electromagnet 62 is excited in a direction by which the magnetic pole 72 of the second electromagnet 62 constitutes S pole and the magnetic pole 73 constitutes N pole. Thereby, the stator pole pieces 53a and 54a are magnetized in G2 direction and the electromagnet 42 of the mover 40 magnetized in B1 direction, and the mover 40 is exerted with attractive force in B1 direction by the stator pole piece 53b magnetized such that a front end side region thereof in G1 direction constitutes S pole, at the front end N pole and is moved in B1 direction by E/2. Further, when the mover 40 is moved from the initial position in B1 direction even slightly, attractive force exerted to S pole of the magnet 42 of the mover 40 by N pole of an end portion in G2 direction of the stator pole piece 54a magnetized in G2 direction, is increased and the force also constitutes to moving the mover 40 in B1 direction by E/2.

Also in this case, when two magnetic poles of the permanent magnet 42 of the mover 40 reach positions opposed to the stator pole pieces 53b and 54a, a force for hampering further displacement is exerted by the two pole pieces and accordingly, the mover 40 is not further moved in B1 direction.

When desired, next, by carrying out similar power feed control except that excitation of the second electromagnet 62 is stopped and the first electromagnet 61 is excited in G1 direction, the mover 40 is further moved in B1 direction by E/2.

In accordance with movement to a state in which the mover 40 is moved from the initial state in B1 direction at intervals of pitch E/2, the projection 41 of the mover 40 reaches a position shifted from the position under the initial state in B1 direction by a distance E/2 multiplied by an integer. Therefore, the doubly supported spring 34 the end portion 32 of which is fixed and the end portion 33 of which is supported by the pole 20, is flexed downwardly and supported at a position further displaced in B1 direction. As a result, the press force exerted to the ball 20 is increased by a predetermined magnitude specified by the position and is set and controlled such that the pressure P of the cerebrospinal fluid in the upstream side cerebrospinal fluid conduit 5a is maintained at a high state by that amount. That is, after the pressure of the cerebrospinal fluid exerted to the ball 20 has been brought into a higher state, the opening 17 is opened and the cerebrospinal fluid in the upstream side cerebrospinal fluid conduit 5a is discharged to the downstream side cerebrospinal fluid conduit 5b.

In the example of FIG. 1, by moving the mover 40 in B1 direction, with regard to the doubly supported spring 34, a distance between the projection 41 of the mover 40 and the end portion 33 is reduced by a unit of E/2 and a distance between the projection 41 and the end portion 32 is increased by the unit of E/2. As a result, in accordance with movement of the mover 40 in B1 direction by the unit of E/2, the press force exerted to the ball 20 by the spring 34 is increased superlinearly. In addition thereto, in the example of FIG. 1, the direction of extending the spring 34 is not in parallel with the moving direction B of the projection 41 of the mover 40. That is, the more proximate to the end portion 33 from the end portion 32, the more upward the spring 34 is disposed in view of FIG. 1. Therefore, according to the example of FIG. 1, in accordance with movement of the mover 40 in B1 direction, a degree of superlinear increase of the press force exerted to the ball 20 by the spring 34 is large.

The degree of increase of the press force can previously be set and adjusted by changing a shape of an upper face 34a of the spring 34 in a state in which external force is not exerted to the spring 34, that is, in a state in which the spring 34 is not pressed by the projection 41.

More in details, at least one of thickness, width, inclination and contour line of the upper face of the spring 34 may be changed in accordance with portions of the spring 34 in B direction such that way of varying the press force of the ball 20 in accordance with movement of the projection 41 in B direction constitutes a desired pattern. In this case, the way of varying the press force may be constituted such that the press force exerted to the ball 20 by the spring 34 is increased actually linearly or increased sublinearly in accordance with movement of the mover 40 in B1 direction. Further, the degree of increase (for example, inclination in linear case) may be made comparatively large or small.

For example, with regard to the width of the spring 34, the width may be constituted such that, for example, the more proximate to the end portion 33, the larger the width, or conversely, the smaller the width, or the width may be varied along the longitudinal direction by other mode (for example, in a range from a predetermined position to the end portion 33, the more proximate to the end portion 33, the larger the width or the width is large at a central portion in B direction and small on both end sides, or the width is small at the central portion in B direction and large at the both end sides, or the width is varied periodically at pitch E/2 or at a period larger or smaller than the pitch E/2 along B direction or the like). The same goes with the thickness and the thickness may be varied along the longitudinal direction instead of or along with varying the width of the spring 34 or the thickness may be varied in the above-described mode. A total of the thickness in the width direction may be varied or a portion of the thickness in the width direction may be varied such that a projected shape or a recess groove extended in a desired range along the longitudinal direction is provided. Further, the spring 34 may be fabricated such that while the thickness stays substantially in a constant state, in view of a cross-sectional face orthogonal to the longitudinal direction, a recess portion is formed at one face and a projected portion is formed at other surface. With regard to the inclination, in the case in which the spring 34 is formed in a flat plate shape, a relative height between the end portion 32 and 33 in FIG. 1 is changed and the spring 34 may be extended in a direction actually in parallel with the B direction or may be inclined slightly in a direction counter to that in the case of FIG. 1. The change of the inclination of the spring in the flat plate shape becomes change of contour of the upper face of the spring. Meanwhile, the contour of the upper face may be changed by changing the thickness of the spring. The above-described change increases or reduces a spring constant K with regard to flexing or bending deformation of the spring 34 in C direction and changes a way of varying the spring constant K depending on the fulcrum position D of the spring 34.

Figure 4:
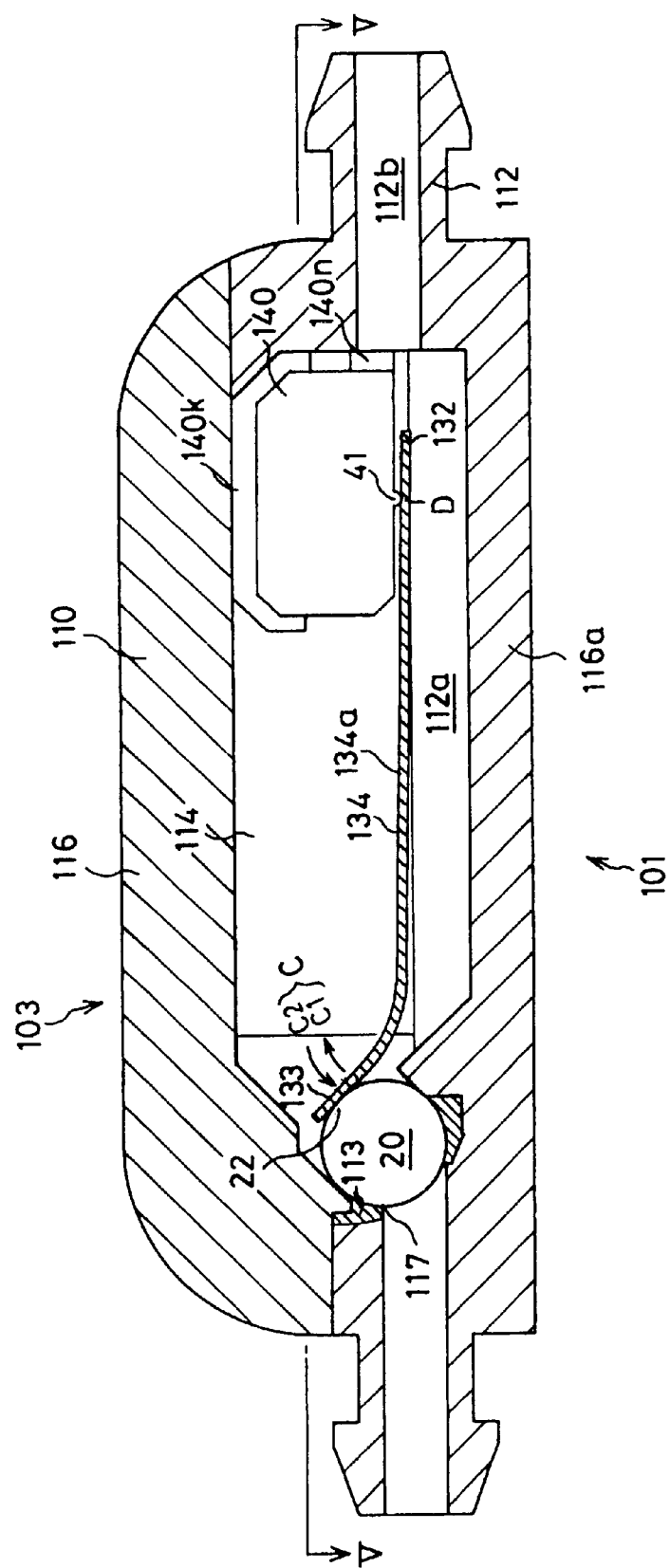
FIG. 4 shows a section similar to that of FIG. 1 in a state before applying a valve system of other preferable embodiment according to the invention to the human body and is an explanatory view of a section taken along a line IV—IV of FIG. 5.

Next, an explanation will be given of a valve system 101 according to other embodiment in reference to FIGS. 4 through 6. In the valve system 101, elements, members and portions the same as or similar to those in the valve system 1 are attached with the same notations and actually corresponding elements, members and portions are attached with notations added with 1 at first portions thereof.

The valve system 101 differs markedly from the valve system 1 in that in place of the linear step motor element 57 as the step motor element, there is used a rotary step motor element 157 having a rotor 80 and the rotary step motor element is coupled to the mover via a motional direction converting mechanism 81, that a spring 134 is not formed in a flat plate shape but is bent at a vicinity of an end portion 133 and an upper face (surface disposed on upper side in view of FIG. 4) 134a of the spring 134 is extended substantially in parallel with B direction at a central portion of the spring 134 in the longitudinal direction, and that a bottom portion of a second conduit portion 112b in an outlet side conduit portion 112, is disposed above a bottom portion of a first conduit portion 112a. Further, the first conduit portion 112a is in a mode of a groove extended in B direction at an upper face of a bottom wall 116a of a valve housing 110 and an upper portion thereof is opened to a chamber 114 of the valve housing 110. Further, a valve apparatus 103 of the valve system 101 is similar to the valve apparatus 3 of FIG. 1 in that the chamber 114 constitutes a portion of a flow path in cooperation with the conduit portion 112a.

Figure 5:
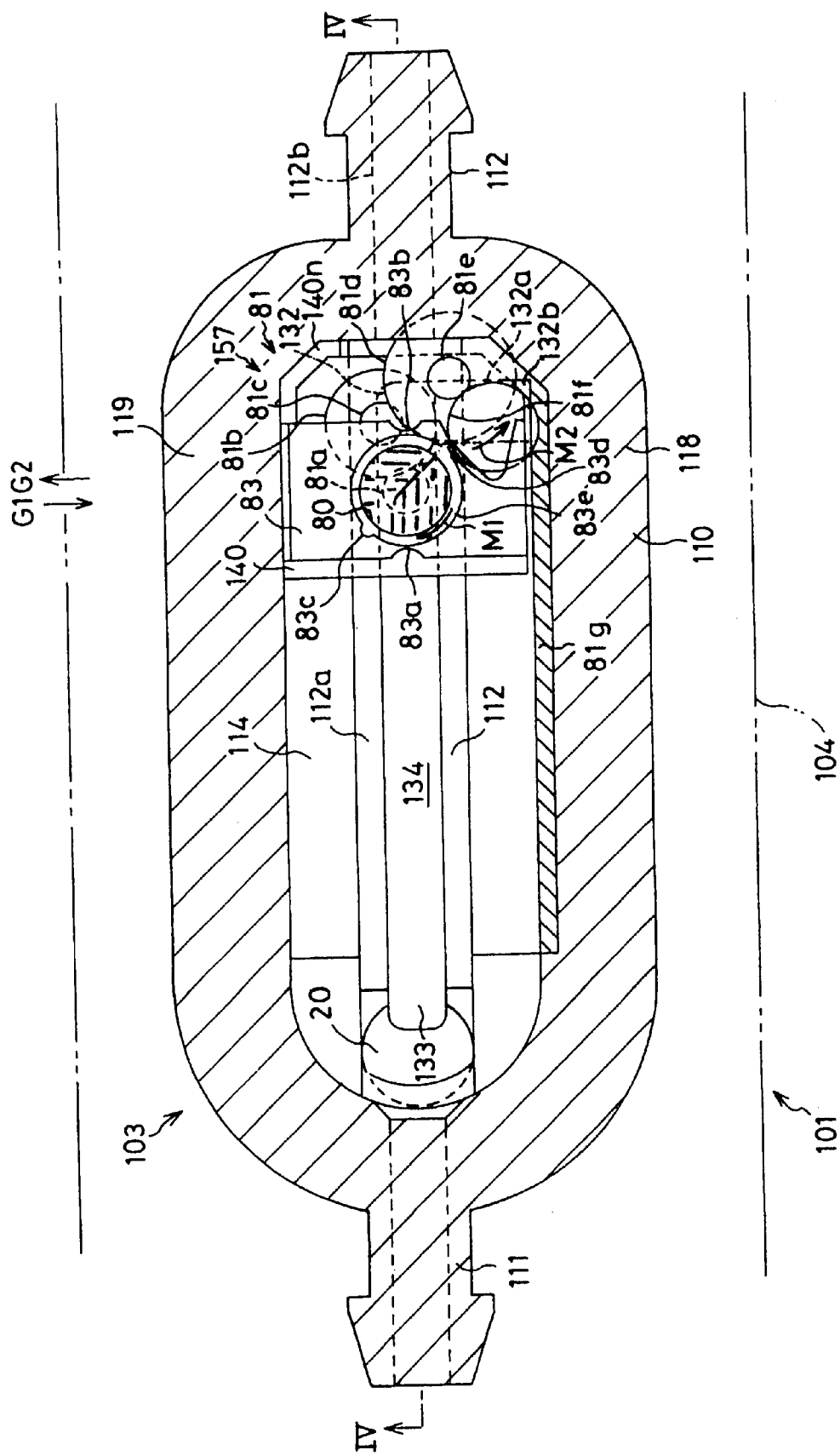
FIG. 5 is an explanatory view of a section taken along a line V—V of the valve system of FIG. 4.
Figure 6:
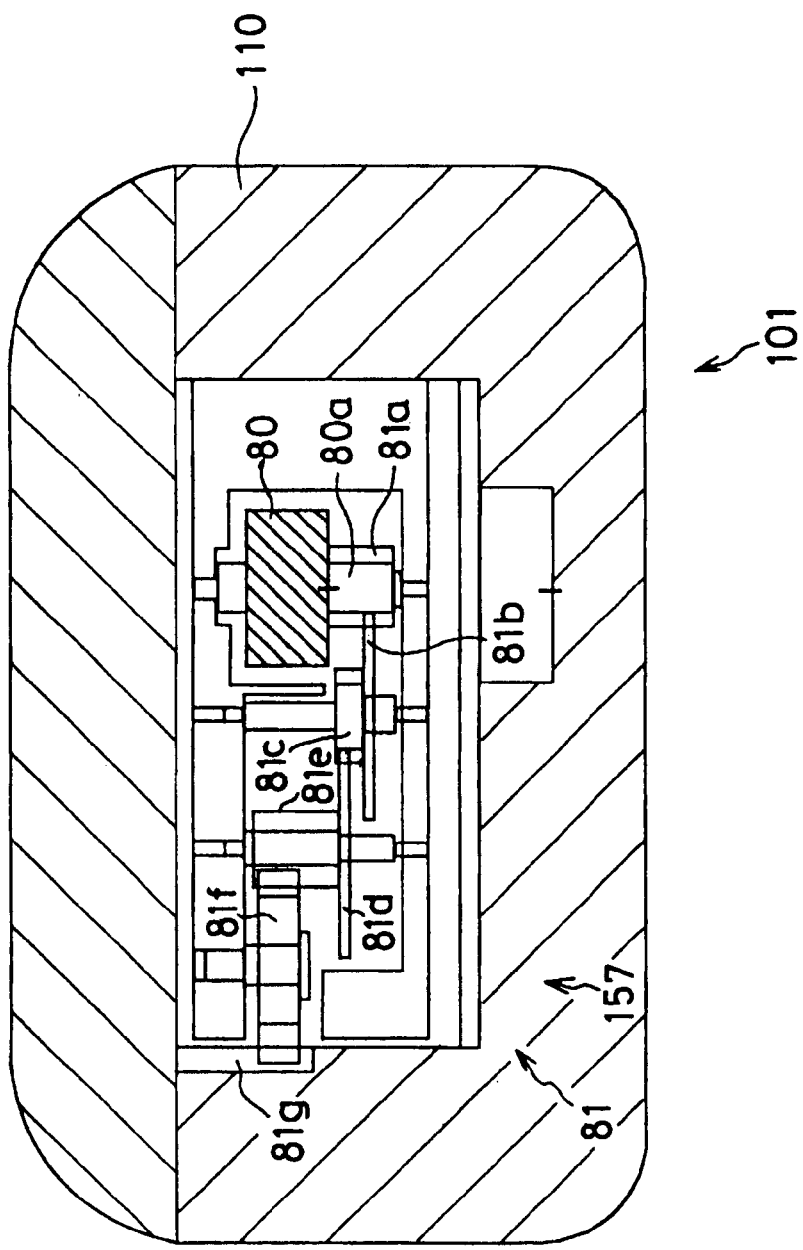
FIG. 6 is an explanatory view of a mechanism for converting rotation motion into translation motion of the valve system of FIG. 4.

More in details, as is apparent from FIG. 5, according to the spring 134 of the valve apparatus 103 of the valve system 101, a base end portion 132 is provided with an arm portion bent in an L-like shape and is fixed to a side wall 118 of a housing 110 at an extended end 132b of the arm portion 132a and the spring 134 is pushed to the upper portion 22 of the ball 20 in C2 direction (FIG. 4) at the other end or front end 133 and is pressed by the projection 41 of a slider 140 at the middle movable fulcrum position D. The base end portion 132 may be provided with a mode of a head portion of "T" as in the valve system 1 of FIG. 1 instead of the arm portion in the L-like shape. The fulcrum may be a rollable ball or the like instead of the projection 41.

The step motor element 157 is typically provided with the rotor 80 in a shape of a circular disk comprising a permanent magnet magnetized in the diameter direction, and a stator 83 having outer notches 83a and 83b for forming magnetically saturated portions at outer side edges thereof and inner notches 83c and 83d specifying a static stable position of the rotor 80 in a direction shifted by 90 degree on a peripheral face of a rotor containing hole 83e and comprising a soft magnetic material having high permeability in a structure known as a step motor for an electronic type analog wrist watch.

According to the step motor element 157, in a state in which the stator 83 is not magnetized, magnetostatic holding force of the rotor 80 is maximized when magnetic poles N and S at both ends in the diameter direction are opposed to peripheral face portions of the hole 83e of the stator 83 where the inner notches 83c and 83d are not present and is held stably at a position where a direction of magnetizing the rotor 80 is directed in a direction orthogonal to a direction connecting the inner notches 83c and 83d. Therefore, even when the human body is vehemently moved and impact force or inertia force is exerted, not only a rotational position of the rotor 80 is difficult to vary but also the rotor 80 is restored to an original position with regard to rotation less than quarter rotation. Meanwhile, when a pulse-like magnetic field having comparatively gradual rise is applied to the stator 83 in a direction (G1 or G2) for moving the rotor 80 disposed at a statically stable position in a direction M1 for moving magnetic poles of the rotor 80 to the outer notches, the rotor 80 is rotated in the M1 direction and reaches a static stable position having a direction different by 180 degree. When the stator 83 is alternately magnetized periodically in G1 direction and G2 direction, the rotor 80 is rotated in M1 direction.

The step motor element 157 may be an element of a step motor of other kind so far as a rotor can be held at a rotational position when a stator is not magnetized by outside magnetic field.

The motional direction converting mechanism 81 is provided with a rotation output gear 81a coaxially formed at an output shaft 80a integral with the rotor 80, a first gear 81b in mesh with the gear 81a, a first pinion 81c coaxial with the gear 81b, a second gear 81d in mesh with the pinion 81c, a second pinion 81e coaxial with the gear 81d, a pinion gear 81f in mesh with the pinion 81e and a rack 81g having rack teeth in mesh with the pinion 81f and extended in B direction. In FIG. 6, the respective gears and pinions are shown in a state of being developed in the left and the right direction of FIG. 6 for easy to see the mesh relationship among the gears 81a through 81f and the rack piece 81g.

According to the motional direction converting mechanism 81, rotation of the rotor 80 is decelerated by mesh of the gears 81a and 81b, the gears 81c and 81d and the gears 81e and 81f and accordingly, at every half rotation of the rotor 80 in the clockwise direction M1 in FIG. 5, the pinion 81f is rotated by a very small angle in the counterclockwise direction M2 and the movable member 140 is moved by a very small amount in B1 direction by being guided by the rack teeth 81g. Further, a number of the gears may be smaller or larger.

Further, in order to rotate the rotor 80 in M2 direction in the step motor element 157 in order to move the movable member 140 in B2 direction, as is known as way of operational control of the motor element 157 of this kind in the field of the electronic type analog timepiece, the rotor is pivoted around a stationary state stabilizing position by a pulse-like magnetic field having small intensity and width and when a direction of magnetizing the rotor 80 exceeds a direction in parallel with G direction and the rotor is pivoted in the reverse direction M2, comparatively large pulse-like magnetic field is applied and the rotor 80 may be rotated in the reverse direction M2 as it is.

Further, in the case in which a failsafe direction of moving the movable member 140 is B2 direction (case of application object in which failsafe operation is directed in a direction of reducing set pressure), positions of the inner notches may be provided on opposite sides and in a normal alternating pulse, the movable member 140 may be moved in B2 direction.

Similar to the movable member 40 of FIG. 1, the movable member 140 is provided with projected portions such as projected portions 140k and 140n at corner portions such that the movable member 140 can be brought into sliding contact with the wall portion 116 or the like of the valve main body 110 at the corner portions and a flowpath is formed between the projected portion. Further, a through hole may be provided at the movable member 140 and the moving direction may be guided by a guide shaft passing through the through hole.

According to the valve system 101 constituted as described above, the movable member 140 can be moved in B1 direction or B2 direction by respective very small distance by mounting a pressure adjusting and controlling device 104 provided with electromagnets similar to the electromagnet 62 at a predetermined position around a region embedded with the valve apparatus main body 110 similar to the case of the pressure adjusting and controlling device 4 in FIGS. 1 and 2 and applying a predetermined pulse-like magnetic field in G direction to the stator 83 of the motor element 157 by the electromagnets.

Further, the electromagnets similar to the electromagnet 62 are provided with shape or arrangement of magnetic poles capable of applying the pulse magnetic field in G direction over an entire range in B direction by which the stator 83 of the movable member 140 can be moved. A number of slender soft magnetic material pieces having high permeability may be embedded to the side walls 118 and 119 of the valve apparatus main body 110 similar to the stator pieces 53 and 54 in order to increase the intensity of the magnetic field applied to the stator 83 by the pressure adjusting and controlling device 104 and to enhance orientation of the magnetic field in G direction.

When the movable member 140 is moved in B1 direction, the position D of the fulcrum pushed by the projection 41 of the movable member 140 is also moved in B1 direction and therefore, the C2 direction press force exerted to the ball 20 by the end portion 133 of the spring 134 is increased and the pressure of the tube path 111 on the upstream side of the opening 117 of the ball valve is adjusted to a high state. Similarly, movement of the valve member 140 in B2 direction constitutes an adjustment in a direction of reducing the adjusted pressure.

What is claimed is:

1. A valve apparatus comprising:
    an elastic member a base end portion of which is fixed and a front end portion of which is brought into contact with a valve element; and
    a movable member movable along a longitudinal direction of the elastic member between both portions of the elastic member and having a fulcrum portion for flexing the elastic member between the both end portions of the elastic member.

2. The valve apparatus according to claim 1, wherein said valve apparatus is constituted to be embedded in a body to adjust a pressure of a fluid.

3. The valve apparatus according to claim 2, wherein said valve apparatus is constituted to adjust a pressure of the cerebrospinal fluid.

4. The valve apparatus according to claim 1, wherein the movable member comprises an element of a linearly driven step motor.

5. The valve apparatus according to claim 4, wherein the step motor element includes a stator constituted to be magnetized in a direction orthogonal to the longitudinal direction of the elastic member.

6. The valve apparatus according to claim 5, wherein the step motor element having a force holding the movable member at a stationary position is produced when the stator is not applied with an outside magnetic field.

7. A valve system comprising:
    the valve apparatus according to claim 6; and
    a movable member position control device for applying a pulse-like magnetic field which is directed in a direction orthogonal to a longitudinal direction of the elastic member and uniform over an entire length of the movable member in a direction of moving the movable member on a stator of a step motor element to move the movable member in the longitudinal direction of the elastic member.

8. The valve system according to claim 7, wherein the movable member position control device is constituted to be arranged at the surface of a body.

9. A valve system comprising:
    the valve apparatus according to claim 5, and
    a movable member position control device for applying a magnetic field which is directed in a direction orthogonal to a longitudinal direction of the elastic member and uniform over an entire length of the movable member in a direction of moving the movable member on a stator of a step motor element to move the movable member in the longitudinal direction of the elastic member.

10. The valve system according to claim 9, wherein the movable member position control device is constituted to be arranged at the surface of a body.

11. The valve apparatus according to claim 1, wherein the movable member is coupled to a converting mechanism for converting rotation of a step motor element of a rotary type into a linear motion.

12. The valve apparatus according to claim 11, wherein the step motor element includes a stator constituted to be magnetized in a direction orthogonal to the longitudinal direction of the elastic member.

13. The valve apparatus according to claim 12, wherein the step motor element having a force holding the movable member at a stationary position is produced when the stator is not applied with an outside magnetic field.

14. A valve system comprising:
    the valve apparatus according to claim 13; and
    a movable member position control device for applying a pulse-like magnetic field which is directed in a direction orthogonal to a longitudinal direction of the elastic member and uniform over an entire length of the movable member in a direction of moving the movable member on a stator of a step motor element to move the movable member in the longitudinal direction of the elastic member.

15. The valve system according to claim 14, wherein the movable member position control device is constituted to be arranged at the surface of a body.

16. A valve system comprising:
    the valve apparatus according to claim 12; and
    a movable member position control device for applying a pulse-like magnetic field which is directed in a direction orthogonal to a longitudinal direction of the elastic member and uniform over an entire length of the movable member in a direction of moving the movable member on a stator of a step motor element to move the movable member in the longitudinal direction of the elastic member.

17. The valve system according to claim 16, wherein the movable member position control device is constituted to be arranged at the surface of the body.

* * * * *